US009434651B2

(12) United States Patent
Carden (10) Patent No.: US 9,434,651 B2
(45) Date of Patent: Sep. 6, 2016

(54) METHOD OF FABRICATING HIGH LIGHT TRANSMISSION ZIRCONIA BLANKS FOR MILLING INTO NATURAL APPEARANCE DENTAL APPLIANCES

(75) Inventor: Robin A. Carden, San Juan Capistrano, CA (US)

(73) Assignee: James R. Glidewell Dental Ceramics, Inc., Newport Beach, CA (US)

(*) Notice: Subject to any disclaimer, the term of this patent is extended or adjusted under 35 U.S.C. 154(b) by 681 days.

(21) Appl. No.: 13/481,810

(22) Filed: May 26, 2012

(65) Prior Publication Data

US 2013/0313738 A1  Nov. 28, 2013

(51) Int. Cl.
*A61C 13/00* (2006.01)
*C04B 35/486* (2006.01)
*A61C 5/10* (2006.01)
(Continued)

(52) U.S. Cl.
CPC .............. *C04B 35/486* (2013.01); *A61C 5/10* (2013.01); *A61C 13/0006* (2013.01); *A61C 13/0022* (2013.01); *C04B 35/62635* (2013.01); *A61C 13/083* (2013.01); *C04B 2235/549* (2013.01); *C04B 2235/5454* (2013.01); *C04B 2235/6026* (2013.01); *C04B 2235/6027* (2013.01); *C04B 2235/612* (2013.01)

(58) Field of Classification Search
CPC .............. C04B 41/009; C04B 35/486; C04B 35/62635; B22F 2998/10; B22F 3/11; B22F 3/22; A61K 6/024–6/025; A61C 13/0022; A61C 5/10
USPC .................... 264/16, 86, 299, 636, 637, 651
See application file for complete search history.

(56) References Cited

U.S. PATENT DOCUMENTS

| 4,431,420 | A | * | 2/1984 | Adair .............................. 106/35 |
| 4,769,349 | A | | 9/1988 | Hillig et al. |
| 4,772,436 | A | | 9/1988 | Tyszblat |

(Continued)

FOREIGN PATENT DOCUMENTS

| DE | 1471423 B | 12/1969 |
| EP | 0329284 | 9/1992 |

(Continued)

OTHER PUBLICATIONS

International Search Report in International Application No. PCT/US2013/041941 mailed Oct. 24, 2013.

(Continued)

*Primary Examiner* — Nahida Sultana
(74) *Attorney, Agent, or Firm* — Dianne Burkhard (57) ABSTRACT

A process for fabricating pre-sintered zirconia blanks that are then computer machined and sintered to form dental appliances having highly advantageous features. The principal steps of a preferred embodiment of that process comprise a) preparing a ceramic slurry of binderless zirconia powder; b) subjecting the slurry to attrition milling down to about a 5-29 nm crystallite size; c) preparing a vacuum assisted and pressure assisted slip casting mold and pouring the milled slurry into the slip-casting mold; d) after casting, excess slurry is poured from the mold and a consolidated zirconia blank is removed; e) drying the blank and pre-sintering it to form solid blanks ready for CAD/CAM machining and sintering to net shape. The attrition is run with ball bearings that are of the sample material to prevent contamination. It also is run, up to 24 hours, to break down the crystallites to overcome the high density of zirconia.

20 Claims, 6 Drawing Sheets

(51) Int. Cl.
  *C04B 35/626* (2006.01)
  *A61C 13/083* (2006.01)

(56) References Cited

U.S. PATENT DOCUMENTS

| | | | | |
|---|---|---|---|---|
| 4,828,495 | A * | 5/1989 | Bell et al. | 433/200.1 |
| 5,203,936 | A * | 4/1993 | Dolhert | B32B 18/00 |
| | | | | 156/89.27 |
| 5,256,609 | A * | 10/1993 | Dolhert | C04B 35/63408 |
| | | | | 156/89.27 |
| 5,296,175 | A | 3/1994 | Iwasaki et al. | |
| 5,342,564 | A * | 8/1994 | Wei | C04B 35/117 |
| | | | | 264/656 |
| 5,372,178 | A * | 12/1994 | Claar | C04B 35/56 |
| | | | | 164/108 |
| 5,395,437 | A | 3/1995 | Chiou | |
| 5,441,408 | A | 8/1995 | Moschik | |
| 5,443,770 | A | 8/1995 | Kristic et al. | |
| 5,672,055 | A | 9/1997 | Koutavas | |
| 5,785,911 | A | 7/1998 | Willkens et al. | |
| 5,788,891 | A * | 8/1998 | Gauckler et al. | 264/86 |
| 5,849,068 | A * | 12/1998 | Hofmann et al. | 106/35 |
| 5,975,905 | A | 11/1999 | Kim et al. | |
| 6,007,926 | A | 12/1999 | Provenzano et al. | |
| 6,291,378 | B1 * | 9/2001 | Evans | A61C 5/10 |
| | | | | 106/35 |
| 6,431,800 | B1 | 8/2002 | Suzuki | |
| 6,878,456 | B2 | 4/2005 | Castro | |
| 6,896,846 | B1 * | 5/2005 | Varma | C22B 5/04 |
| | | | | 419/45 |
| 6,946,013 | B2 * | 9/2005 | Alward et al. | 55/523 |
| 8,178,012 | B1 * | 5/2012 | Khan | A61C 13/082 |
| | | | | 264/16 |
| 8,268,230 | B2 * | 9/2012 | Cherepy | B82Y 30/00 |
| | | | | 264/621 |
| 9,039,947 | B2 * | 5/2015 | Jahns | A61C 13/0003 |
| | | | | 264/16 |
| 2001/0048969 | A1 | 12/2001 | Constantino et al. | |
| 2002/0037800 | A1 * | 3/2002 | Yang | 501/87 |
| 2003/0096214 | A1 | 5/2003 | Luthardt et al. | |
| 2004/0119180 | A1 | 6/2004 | Frank et al. | |
| 2005/0023710 | A1 * | 2/2005 | Brodkin | A61C 13/0003 |
| | | | | 264/16 |
| 2005/0203231 | A1 | 9/2005 | Halpert et al. | |
| 2006/0014390 | A1 | 1/2006 | Lee et al. | |
| 2007/0056467 | A1 | 3/2007 | Panzera | |
| 2007/0134496 | A1 | 6/2007 | Katagiri et al. | |
| 2008/0085828 | A1 * | 4/2008 | Khan et al. | 501/152 |
| 2008/0164402 | A1 * | 7/2008 | Menke | B28B 1/261 |
| | | | | 249/102 |
| 2008/0258358 | A1 * | 10/2008 | Oswald et al. | 264/651 |
| 2009/0098365 | A1 * | 4/2009 | Moeltgen | B82Y 30/00 |
| | | | | 428/328 |
| 2009/0115084 | A1 * | 5/2009 | Moon | 264/16 |
| 2009/0220787 | A1 * | 9/2009 | Bernard-Granger et al. | 428/402 |
| 2009/0291011 | A1 | 11/2009 | Zhang et al. | |
| 2009/0321971 | A1 * | 12/2009 | Brodkin et al. | 264/17 |
| 2010/0003157 | A1 * | 1/2010 | Scholl et al. | 419/23 |
| 2011/0236860 | A1 * | 9/2011 | Jahns | C04B 35/486 |
| | | | | 433/222.1 |
| 2011/0260349 | A1 | 10/2011 | Rolf et al. | |
| 2012/0193823 | A1 * | 8/2012 | Goetzinger | A61C 13/0003 |
| | | | | 264/16 |
| 2013/0224454 | A1 * | 8/2013 | Jung | A61C 13/0004 |
| | | | | 428/213 |
| 2013/0224688 | A1 * | 8/2013 | Mayr | A61C 5/10 |
| | | | | 433/200.1 |
| 2013/0341812 | A1 * | 12/2013 | Schechner | A61K 6/0094 |
| | | | | 264/17 |

FOREIGN PATENT DOCUMENTS

JP 11019910 A 1/1999
WO WO2006024098 A1 3/2006

OTHER PUBLICATIONS

U.S.P.T.O Non-Final Office Action issued in U.S. Appl. No. 12/290,089 dated Jun. 2, 2009.
U.S.P.T.O Non-Final Office Action issued in U.S. Appl. No. 12/290,089 dated Dec. 1, 2009.
International Search Report issued in application PCT/US2008/12489 dated Dec. 31, 2008.

* cited by examiner

METHOD OF FABRICATING HIGH LIGHT TRANSMISSION ZIRCONIA BLANKS FOR MILLING INTO NATURAL APPEARANCE DENTAL APPLIANCES

BACKGROUND OF THE INVENTION

1. Field of the Invention

The present invention relates generally to the manufacture of ceramic dental appliances such as crowns and bridges. The invention herein is related more particularly to the milling of zirconia blanks into such appliances where the blanks are fabricated by a vacuum and pressure assisted slip-casting method to achieve superior physical properties.

2. Background Art

Dental prosthetic devices or appliances must satisfy a number of different criteria. They need to have excellent physical properties (Flexural Strength to 1600 MPa) to resist wear and mechanical deformation for very long periods of time. They should also provide good aesthetic characteristics which means that they have a natural appearance in color, texture and shape so that they are not readily distinguishable from the original natural teeth. They should also be readily fabricated at reasonable cost which means that the cost of materials used and the time required in their manufacture, should be within reasonable limits.

Dental appliances made of zirconia can meet these criteria. It is a ceramic material which can be made to be extremely hard and fracture resistant. Applicant has discovered that if provided in pre-fabricated pre-sintered blanks, they can be readily machined in CAD/CAM systems and then sintered with highly predictable shrinkage to conform to virtually any desired dental appliance shape with high yield and minimal manual intervention. A key aspect of the aesthetic appearance of zirconia dental appliances would be achieved if it were possible to provide such prosthetic devices with a substantial degree of light transmissivity. Translucent appliances would exhibit the color of the underlying natural dental material and thus go a long way toward achieving a highly desirable appearance, i.e., that is matched to the color of adjacent natural teeth. Thus, if it were possible to provide pre-fabricated, pre-sintered zirconia blanks and yet still retain the advantageous mechanical and easy fabrication properties of the ceramic, that would be a significant accomplishment in the art of dental appliances. Even though Applicant is not the first to consider slip-casting zirconia for the dental appliance art (see U.S. Pat. No. 4,772,436 to Tyszblat or U.S. Pat. No. 5,975,905 to Kim et al), there is no known relevant prior art which discloses all of the process steps of the present invention for fabricating a pre-sintered zirconia blank for the dental appliance arts. Moreover, Tyszblat teaches the interlacing of fitted metal oxide particles in the solid phase and glass. Kim et al discloses the creation of a ceramic sheet of thickness 0.1 mm to 1.0 mm and then coating the sheet onto a gypsum mold under heat and pressure and then, after sintering, coating the resultant body with glass powder. No other known partially stabilized zirconia material can be made to reach a stiffness of 1600 MPa mark when slip cast. No other known partially stabilized zirconia material reaches the high degree of light transmission in the 500-800 nm wavelength, which is needed to transmit the warm colors of the mouth. The partially stabilized zirconia is normally very hard to slip cast with a high density of 6.03 g/cc. Aluminum oxide for example is readily slip cast because of its lower density 3.98 g/cc. Any ceramic with density between 2.0 and 4.0 g/cc is more readily made by a slip cast process. This is because the lower density allows the particulate to stay dispersed longer which results in better green density and strength after final sintering. When densities rise above 4 g/cc, high strength is never reached in colloidal processing. Very high density materials normally cannot be cast at all, such as tungsten carbide at 14.6 g/cc.

SUMMARY OF THE INVENTION

The present invention comprises a process for fabricating pre-sintered zirconia blanks that are then computer machined and sintered to form translucent dental appliances having highly advantageous features. The principal steps of a preferred embodiment of that process comprise a) preparing a ceramic slurry of binderless zirconia powder; b) subjecting the slurry to attrition milling for an extended time of up to 24 hours to achieve a crystallite size in the range of about 5 nm to about 29 nm; c) preparing a vacuum assisted and optional pressure assisted slip casting mold and pouring the milled slurry into the slip-casting mold; d) after casting, excess slurry is poured from the mold and a consolidated zirconia blank is removed; e) drying the blank and pre-sintering it to form solid blanks ready for CAD/CAM machining and sintering to net shape. In the preferred embodiment of the process herein, the zirconia powder is dispersed in deionized water using a dispersant chemical solution such as tetramethyl ammonium hydroxide to adjust the pH of the slurry and thus homogeneously disperse the zirconia powder. Other dispersants such as polyisobutylene, various acid salts, bases and certain oils, may also serve as dispersant chemicals. The present invention achieves extremely high flexural strength and unusually high translucency by employing zirconia fabricated by a slip cast method in which the crystallite size is in the range of about 5 nm to about 29 nm to overcome the inherent high density of zirconia. The uniquely achieved flexural strength and translucency are particularly important in the field of dental restorations such as crowns and bridges where resistances to bite pressure and material appearance are critical.

BRIEF DESCRIPTION OF THE DRAWINGS

The aforementioned objects and advantages of the present invention, as well as additional objects and advantages thereof, will be more fully understood herein after as a result of a detailed description of a preferred embodiment when taken in conjunction with the following drawings in which.

DETAILED DESCRIPTION OF A PREFERRED EMBODIMENT

Figure 1:
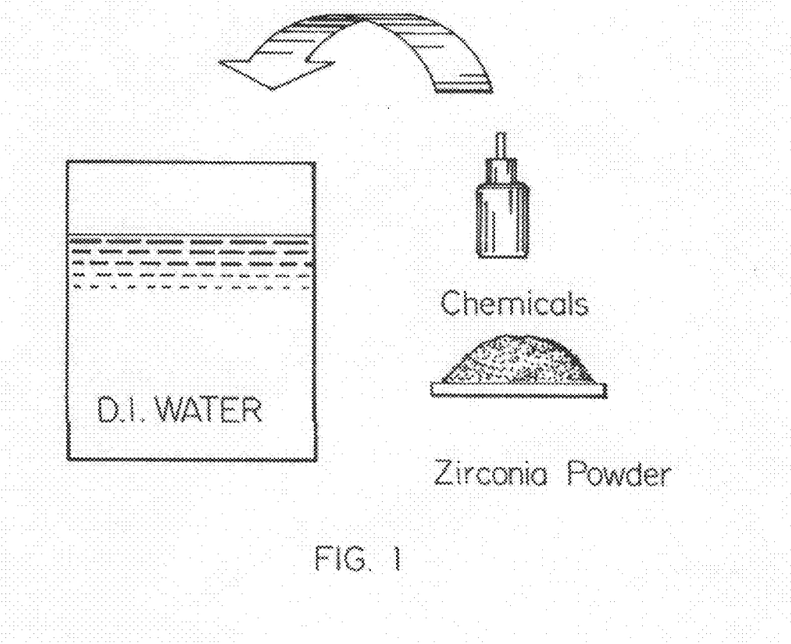
FIG. 1 shows the slurry preparation process by mixing zirconia powder and chemicals (either a dispersant or a chemical that controls PH) into deionized water.
Figure 2:
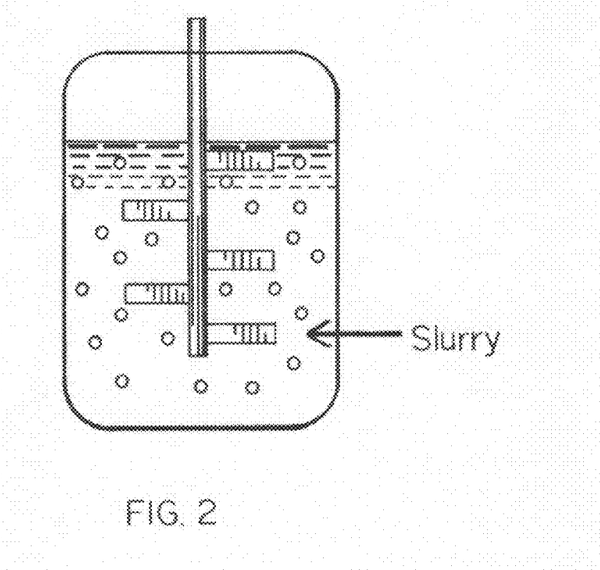
FIG. 2 represents the attrition milling step.
Figure 3:
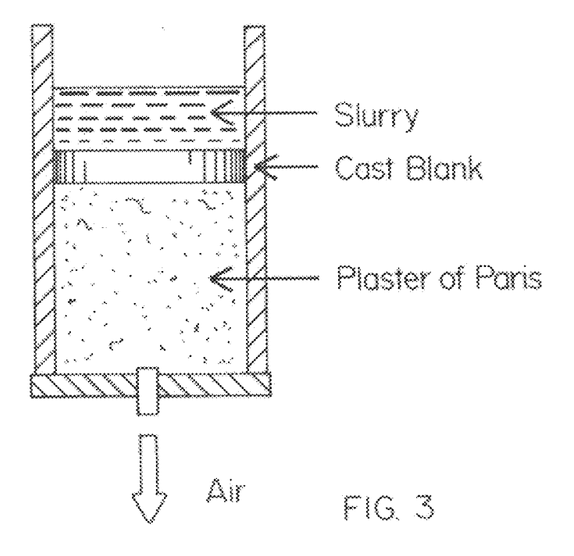
FIG. 3 represents the vacuum slip casting step of the invention.
Figure 4:
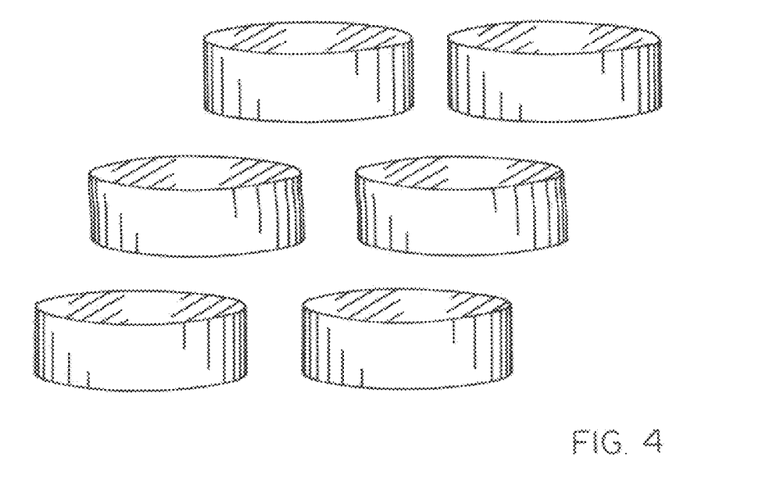
FIG. 4 shows the drying step of the invention.
Figure 5:
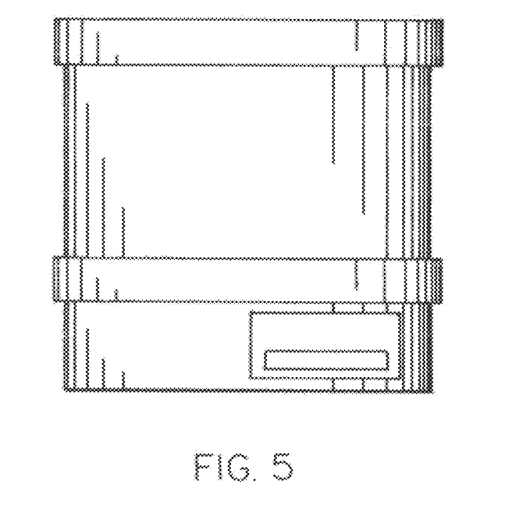
FIG. 5 shows the pre-sintering step of the inventive process hereof.
Figure 6:
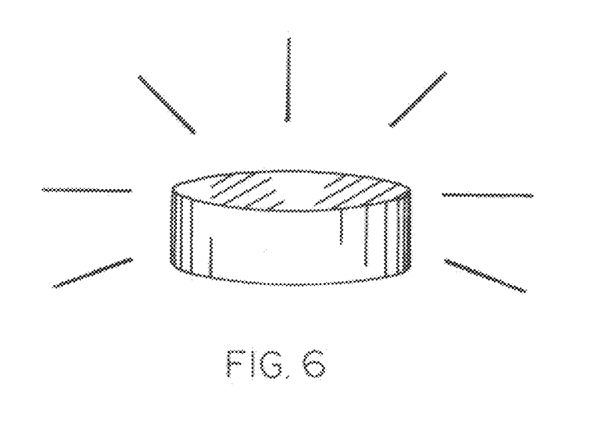
FIG. 6 represents the completed pre-sintered zirconia blank ready to be machined in a CAD/CAM system.
Figure 7:
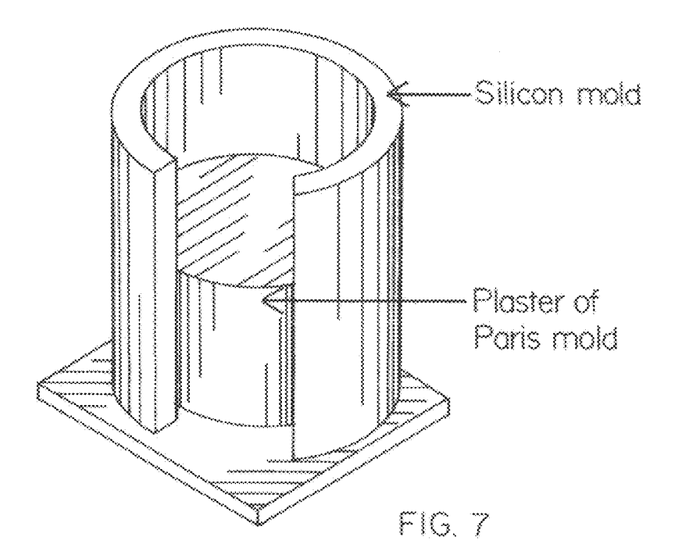
FIGS. 7 to 8 illustrate in some added detail, the slip-casting step of FIG. 3.
Figure 8:
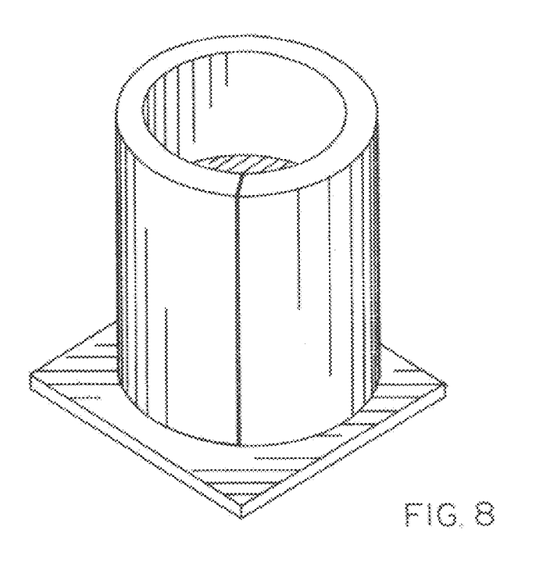

Referring to the accompanying drawings and initially to FIGS. 1 to 6, it will be seen that the present invention is a process comprising the following steps:

a) The zirconia powder is dispersed into de-ionized water using either polymer dispersants or by controlling pH with base/acid. The slurry is preferably ultra-sonicated to remove soft agglomerates and for better mixing (see FIG. 1).

b) Attrition milling the prepared slurry, preferably in a zirconia bowl (see FIG. 2) until the crystallite size is in the range of about 5 nm to about 29 nm.

c) Slip-casting the milled slurry by preparing a porous plaster of paris mold. An organic polymer mold may be substituted for the plaster of paris mold. Placing the plaster of paris mold within a surrounding silicone mold enclosure (or enclosure of a rubber or other elastic polymer material, see FIGS. 11A and 11B) and softly tightening the enclosure around the plaster of paris to form a leak-proof system (see FIGS. 7 and 8). In the preferred embodiment, the enclosure is secured by rubber bands or pipe ties (see FIG. 9). Attaching to a bottom surface aperture of the enclosure, a vacuum line to suck out excess liquid (i.e., water) (see FIG. 10). A vacuum pressure of −5 to −40 psi is preferred. Pouring the slurry into the enclosure above the plaster of paris mold. Eventually a slip-cast zirconia blank will form above the plaster of paris mold. This blank is removed by pouring out the excess slurry and opening the silicone mold to permit removal of the plaster of paris mold and zirconia blank. An optional positive pressure may be applied above the enclosure to further promote the process. A positive pressure of 1 to 30 psi is preferred.

d) Each removed zirconia blank is allowed to dry at room temperature preferably using gently circulating air at low humidity (see FIG. 4). The zirconia blocks are then pre-sintered at 850° C. to 1200° C. for about two hours (see FIG. 5). The fully dried zirconia blanks are ready for computer-controlled milling and sintering to net shape (see FIG. 6).

Figure 9A:
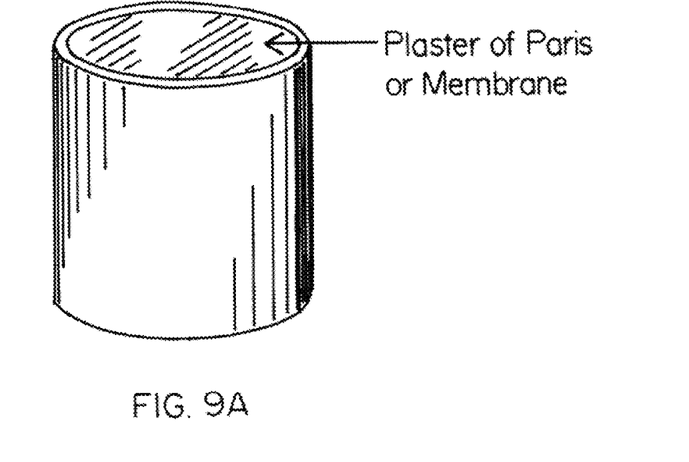
FIGS. 9A and 9B show an optional added slip casting step using a polymer sleeve enclosed plaster of paris mold to protect the delicate plaster of paris material during handling.
Figure 9B:
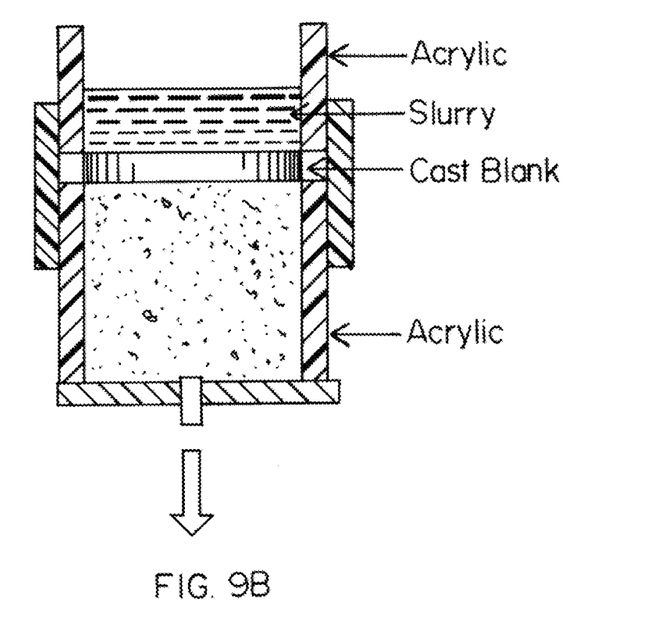

As shown in FIGS. 9A and 9B, the plaster of paris mold may be protected from handling damage by enclosing its radial surface in a plastic or polymer sleeve.

Figure 10:
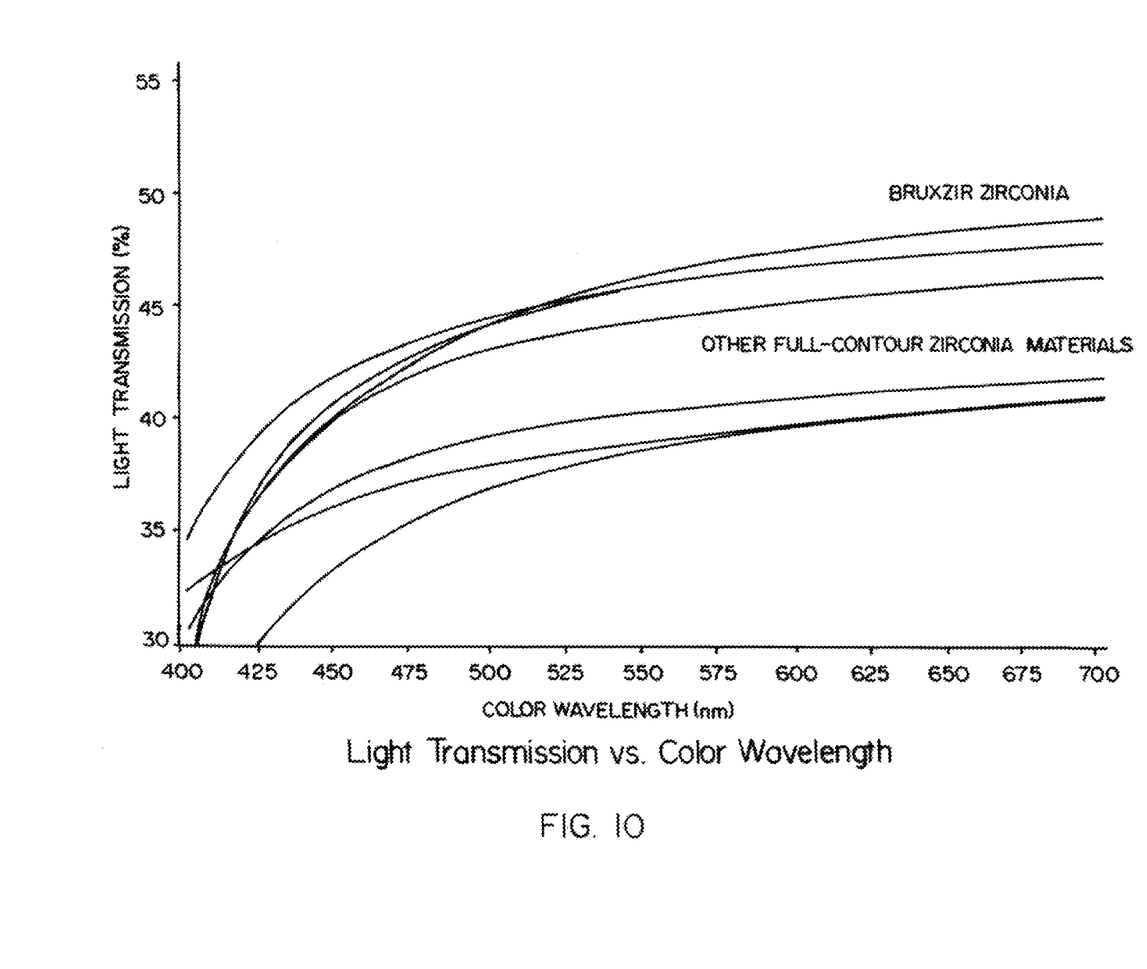
FIG. 10 is a graphical illustration of light transmission versus color wavelength for zirconia that is fabricating using the method of the invention and for zirconia made by more conventional methods.

FIG. 10 shows graphically the favorable light transmission characteristics of zirconia restorations made according to the preferred embodiment hereof and compares such characteristics to more conventionally fabricated zirconia restorations as a function of wavelength.

It will now be understood that the present invention comprises a process for preparing zirconia blanks for milling into dental appliance shapes using CAD/CAM control and then sintering the shaped zirconia appliances to net shape.

Although a preferred embodiment has been disclosed herein, it will now be apparent that various modifications may be made to the various steps hereof without deviating from the principal inventive features hereof. Accordingly, the scope of the invention is to be limited only by the appended claims and to their equivalents.

I claim:

1. A process for fabricating dental appliances of translucent zirconia; the process comprising the steps of:
   a) preparing a ceramic slurry comprising mixing binderless zirconia powder, water and a dispersant;
   b) attrition milling the ceramic slurry to a crystallite size in the range of about 5 nm to about 29 nm;
   c) slip casting the milled ceramic slurry in a vacuum-assisted mold;
   d) removing water from the milled ceramic slurry and consolidating the zirconia powder to form zirconia blanks by subjecting one end of the vacuum-assisted mold to an evacuating pressure in a range of −5 to −40 psi and subjecting another end of the vacuum-assisted mold to a positive pressure in a range of 1 to 30 psi;
   e) removing zirconia blanks formed in said slip casting step;
   f) allowing the zirconia blanks to dry;
   g) pre-sintering the dried zirconia blanks to form dried, pre-sintered zirconia blanks;
   h) shaping the dried, pre-sintered zirconia blanks into appliance-shaped blanks; and
   i) sintering the appliance-shaped blanks to net shape and size.

2. The process recited in claim 1 wherein the step of preparing the ceramic slurry comprises dispersing zirconia powder in tetra ethyl ammonium hydroxide.

3. The process recited in claim 1 wherein the vacuum-assisted mold comprises a polymer sleeve in a radial surrounding engagement with a plaster of paris mold.

4. The process recited in claim 1 wherein step a) is performed by dispersing the zirconia powder in deionized water.

5. The process recited in claim 4 wherein the step of preparing the slurry comprises dispersing zirconia powder in acid with pH of 1-3.9.

6. The process recited in claim 1 wherein step a) comprises the additional step of ultra-sonicating the ceramic slurry to remove soft agglomerates for improved mixing of the powder zirconia.

7. Process recited in claim 1 wherein step b) is performed using a zirconia bowl.

8. The process recited in claim 1 wherein step g) is performed at a temperature in the range of about 850° C. to 1200° C.

9. The process recited in claim 1 wherein the pre-sintering step is conducted at a temperature in the range of about 850° C. to 1200° C. for about two hours.

10. A process for forming zirconia blanks for use in fabricating dental appliances; the process comprising the steps of:
   a) preparing a slurry of zirconia powder dispersed by chemical dispersants in deionized water;
   b) attriting the slurry to form a homogeneous, mixed slurry having a range of crystallite sizes of about 5 nm to about 29 nm;
   c) pouring the mixed slurry into a vacuum-assisted assembly;
   d) removing water from the milled slurry and consolidating the zirconia powder to form zirconia blanks by subjecting one end of the vacuum-assisted assembly to an evacuating pressure from −5 to −40 psi and another end of the vacuum-assisted assembly to a positive pressure of from 1 to 30 psi;
   e) removing said zirconia blanks from the vacuum-assisted assembly;

f) subjecting said zirconia blanks to a presintering temperature to achieve partial densification of said zirconia blanks.

11. The process recited in claim 10 wherein the dispersant comprises tetramethyl ammonium hydroxide.

12. The process recited in claim 10 wherein the vacuum-assisted assembly comprises a polymer sleeve in radial surrounding engagement with a plaster of paris mold.

13. The process recited in claim 10 wherein step a) is performed by dispersing the zirconia powder in water by controlled pH.

14. The process recited in claim 10 wherein step a) comprises the additional step of ultra-sonicating the slurry to remove soft agglomerates for improved mixing of the powder.

15. The process recited in claim 10 wherein step b) is performed using a zirconia bowl and attriting for up to 24 hours.

16. The process recited in claim 10 wherein the pre-sintering is performed at a temperature in the range of about 850° C. to 1200° C.

17. The process recited in claim 10 wherein step f) is performed at a temperature in the range of about 850° C. to 1200° C. for about two hours.

18. The process in claim 10 wherein said chemical dispersants in step a) comprises at least one dispersant selected from an acid which comprises a nitric acid, and a base which comprises sodium hydroxide.

19. The process in claim 10 wherein the vacuum-assisted assembly is a slip casting assembly.

20. The process of claim 10 wherein the zirconia blanks are millable blanks.

\* \* \* \* \*

UNITED STATES PATENT AND TRADEMARK OFFICE
CERTIFICATE OF CORRECTION

PATENT NO. : 9,434,651 B2  Page 1 of 1
APPLICATION NO. : 13/481810
DATED : September 6, 2016
INVENTOR(S) : Robin A. Carden It is certified that error appears in the above-identified patent and that said Letters Patent is hereby corrected as shown below:

IN THE SPECIFICATION

Column 4 line 28: the text "powder in tetra ethyl" should read --powder in tetramethyl--

Signed and Sealed this
Fifteenth Day of November, 2016

Michelle K. Lee
*Director of the United States Patent and Trademark Office*